United States Patent
Soroff et al.

[11] Patent Number: 5,938,027
[45] Date of Patent: Aug. 17, 1999

[54] SURGICAL BLADE SYSTEM

[75] Inventors: Harry Soroff, Northport, N.Y.; William McCabe, New Canaan, Conn.; John E. Burbank, Ridgefield, Conn.; Lester F. Miller, Danbury, Conn.; Daniel Shichman, Trumbull, Conn.

[73] Assignee: Stony Brook Surgical Innovations, Inc., Northport, N.Y.

[21] Appl. No.: 08/986,479

[22] Filed: Dec. 8, 1997

[51] Int. Cl.⁶ .................................................. B65D 83/10
[52] U.S. Cl. ...................... 206/370; 206/355; 206/359; 29/239
[58] Field of Search .................... 206/354–358, 206/366, 370, 359, 360; 29/239

[56] References Cited

U.S. PATENT DOCUMENTS

| | | |
|---|---|---|
| D. 264,882 | 6/1982 | Thompson . |
| 3,172,316 | 3/1965 | Grieshaber . |
| 4,106,620 | 8/1978 | Brimmer et al. . |
| 4,120,397 | 10/1978 | Neumann . |
| 4,168,777 | 9/1979 | Gaskell et al. . |
| 4,180,162 | 12/1979 | Magney . |
| 4,270,416 | 6/1981 | Thompson . |
| 4,318,473 | 3/1982 | Sandel . |
| 4,344,532 | 8/1982 | Eldridge, Jr. et al. . |
| 4,378,624 | 4/1983 | Klingenberg . |
| 4,386,457 | 6/1983 | Coombs . |
| 4,395,807 | 8/1983 | Eldridge, Jr. et al. . |
| 4,466,539 | 8/1984 | Frauenhoffer . |
| 4,523,679 | 6/1985 | Paikoff et al. . |
| 4,730,376 | 3/1988 | Yamada . |
| 4,746,016 | 5/1988 | Pollak et al. . |
| 4,903,390 | 2/1990 | Vidal et al. . |
| 4,998,334 | 3/1991 | Pemberton et al. . |
| 5,088,173 | 2/1992 | Kromer et al. . |
| 5,163,553 | 11/1992 | Cantwell et al. . |
| 5,361,902 | 11/1994 | Abiden et al. . |
| 5,406,684 | 4/1995 | Carson . |
| 5,449,068 | 9/1995 | Gharibian . |
| 5,667,067 | 9/1997 | Gabriel ..................................... 206/355 |
| 5,699,908 | 12/1997 | Frye et al. ............................... 206/355 |

FOREIGN PATENT DOCUMENTS

| | | |
|---|---|---|
| 0034949 | 2/1981 | European Pat. Off. . |
| 0242035 | 10/1987 | European Pat. Off. . |
| 2035186 | 6/1980 | United Kingdom . |
| 8300454 | 2/1983 | WIPO . |

*Primary Examiner*—Paul T. Sewell
*Assistant Examiner*—John Preta
*Attorney, Agent, or Firm*—Robert L. Epstein; Harold James; James & Franklin, LLP

[57] ABSTRACT

The handle has a blade mounting portion with a raised boss forming a slot. The blade has a boss receiving recess with a portion defined by an edge. The cartridge removeably retains the blade. It has an opening into which the blade mounting portion of the handle can be inserted. A normally arcuate spring is mounted in cantilever fashion within the enclosure. The tip of the blade abuts a stop surface proximate the unattached end of the spring. In its arcuate state, the spring retains the blade in a position where the edge of the blade can enter the slot in the handle. As the blade is moved by insertion of the handle, against the urging of the spring, the spring straightens allowing the blade to assume a position where the boss can be fully seated within the recess, mounting the blade on the handle. The blade is then removed from the cartridge by withdrawing the handle. After use, the blade is reinserted into the cartridge. A pushbutton, accessible from the exterior of the cartridge, is depressed to cause the boss to withdraw from the slot to dismount the blade from the handle. A stand for retaining multiple cartridges is provided. Each cartridge is supported by a rigid finger aligned with the pushbotton. Applying a downward force on the cartridge causes the pushbutton to depress to dismount the blade.

23 Claims, 8 Drawing Sheets

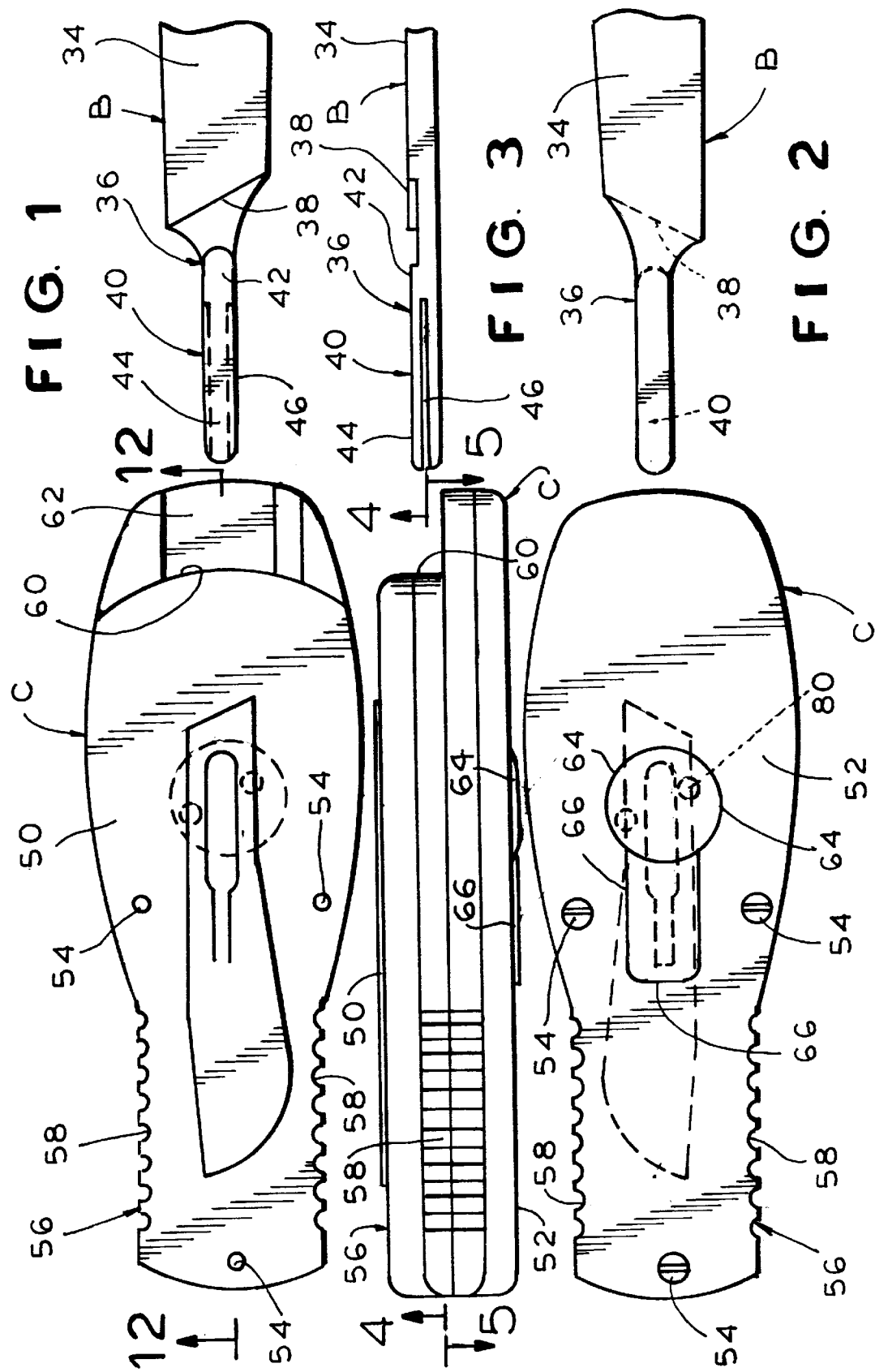

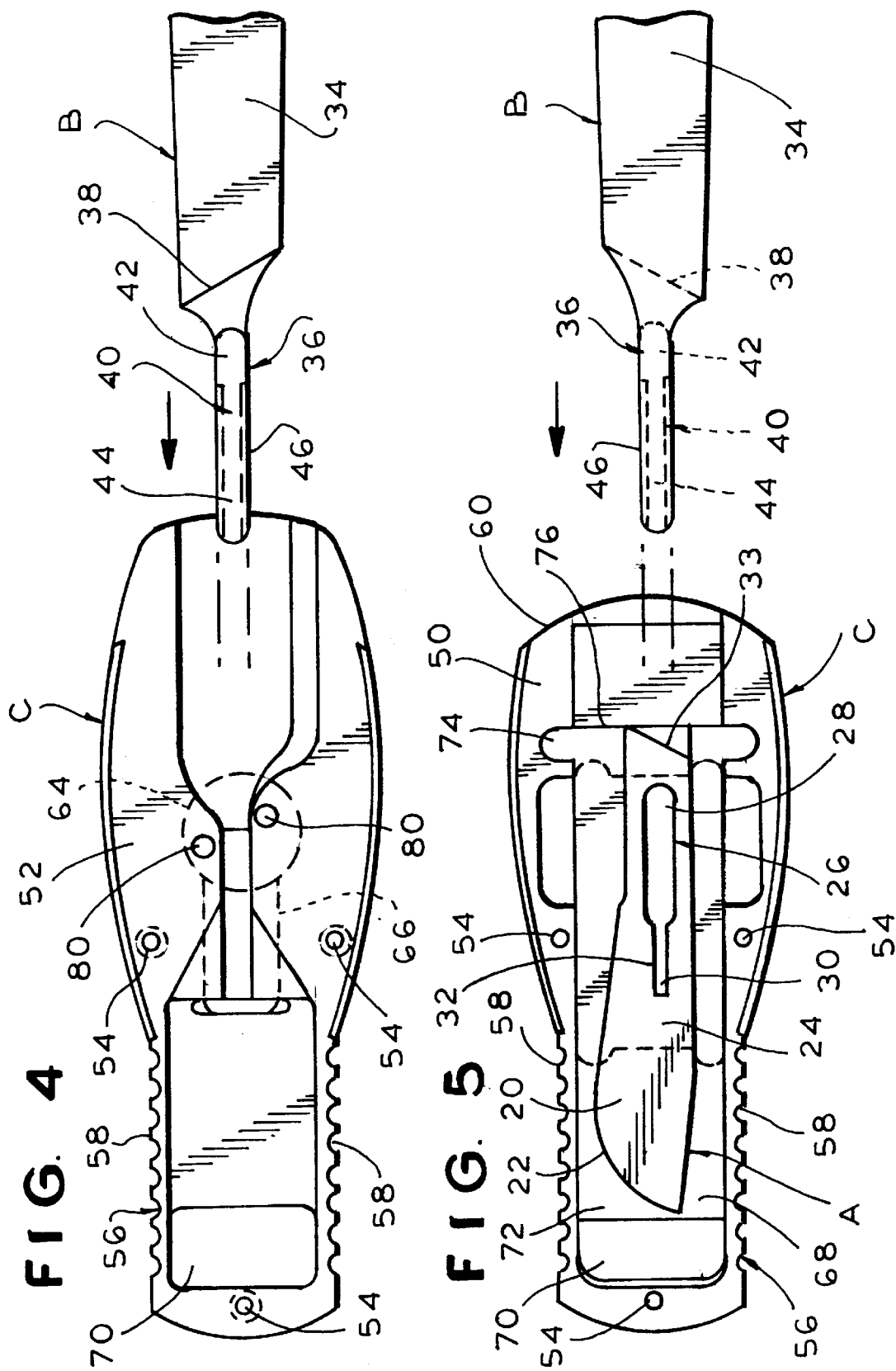

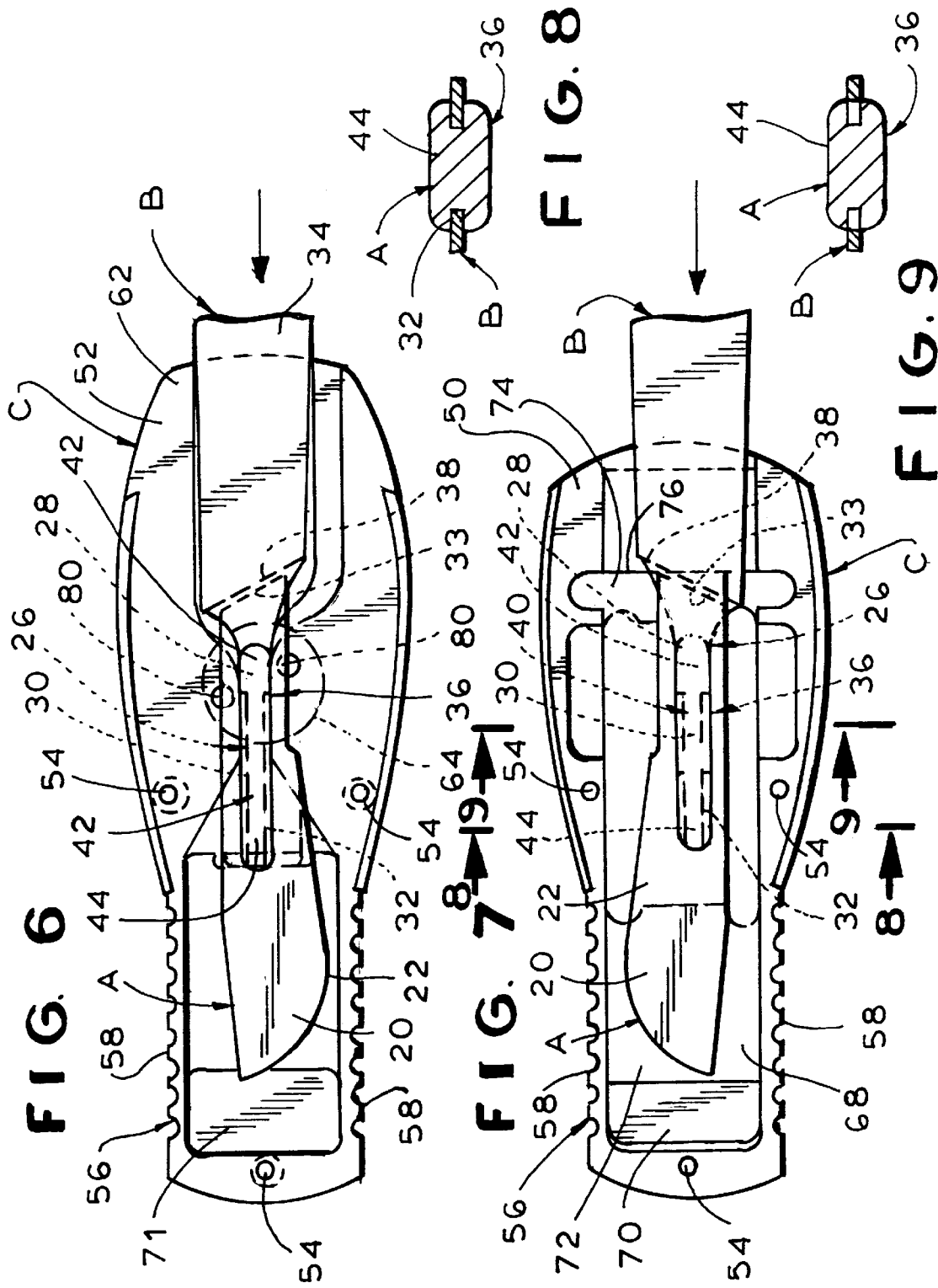

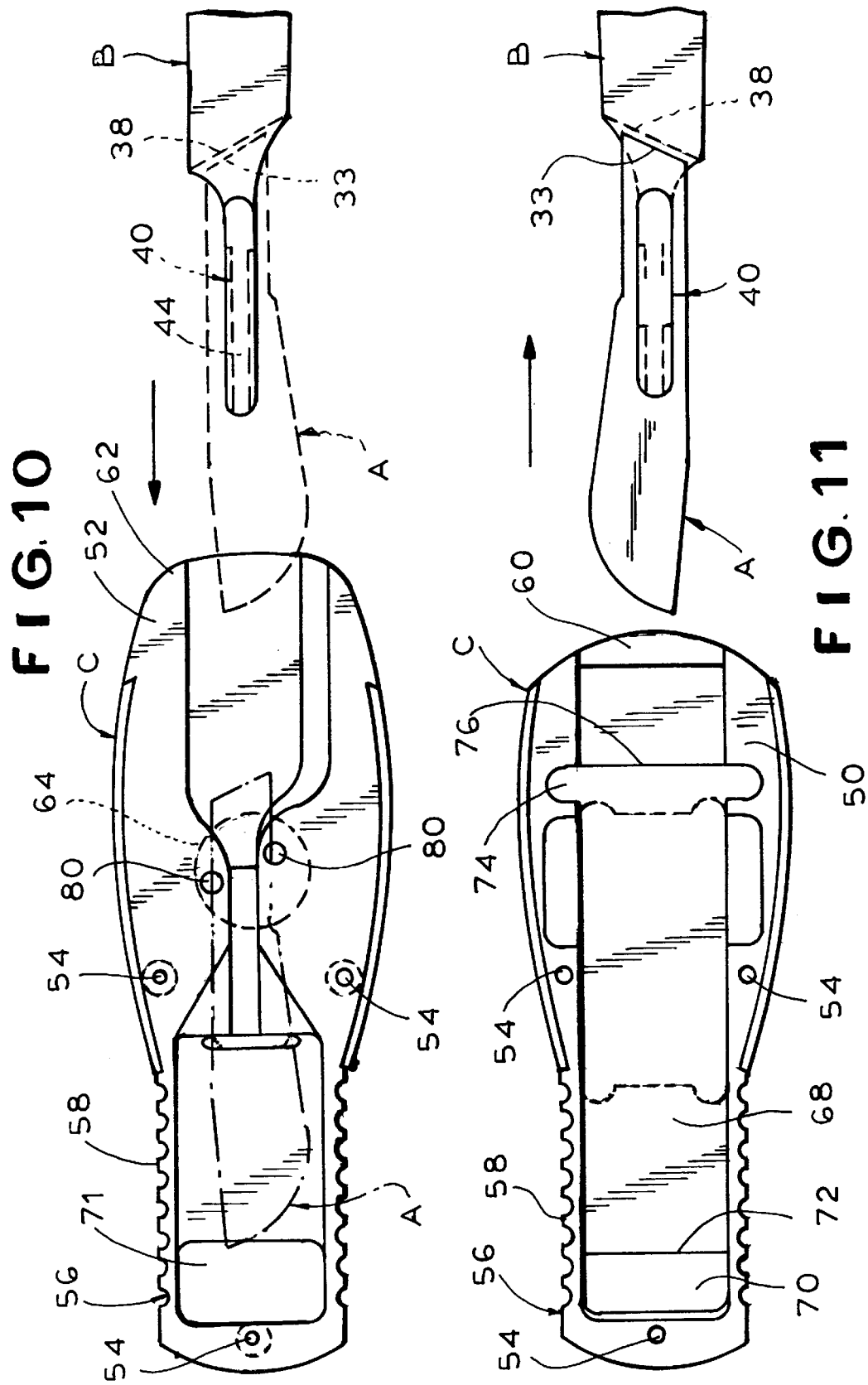

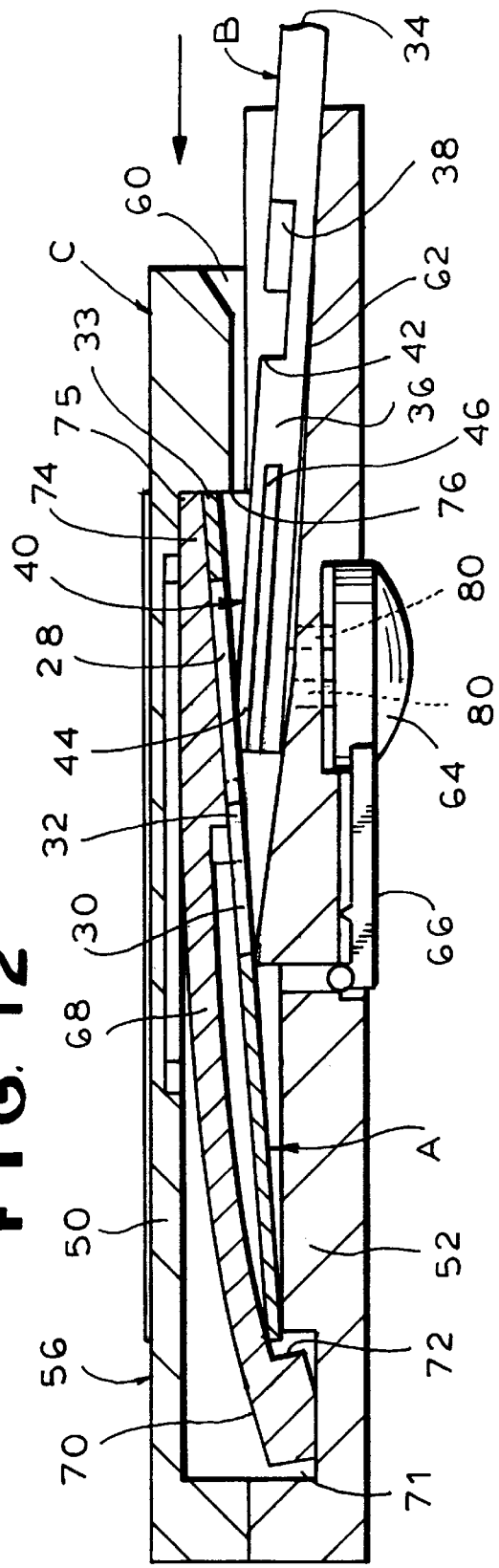
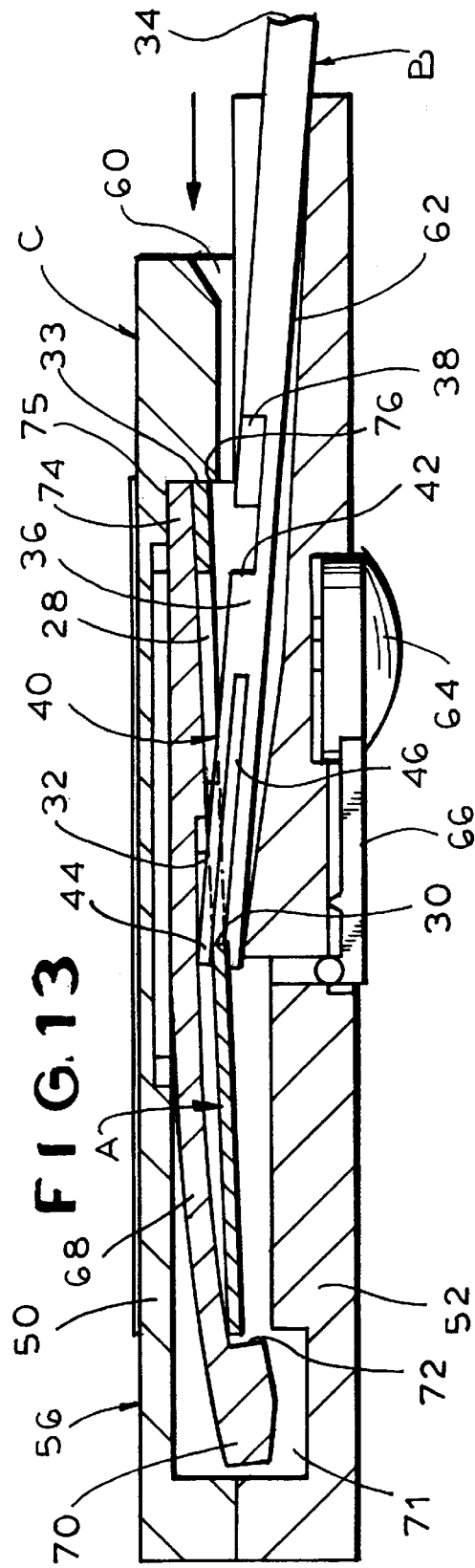

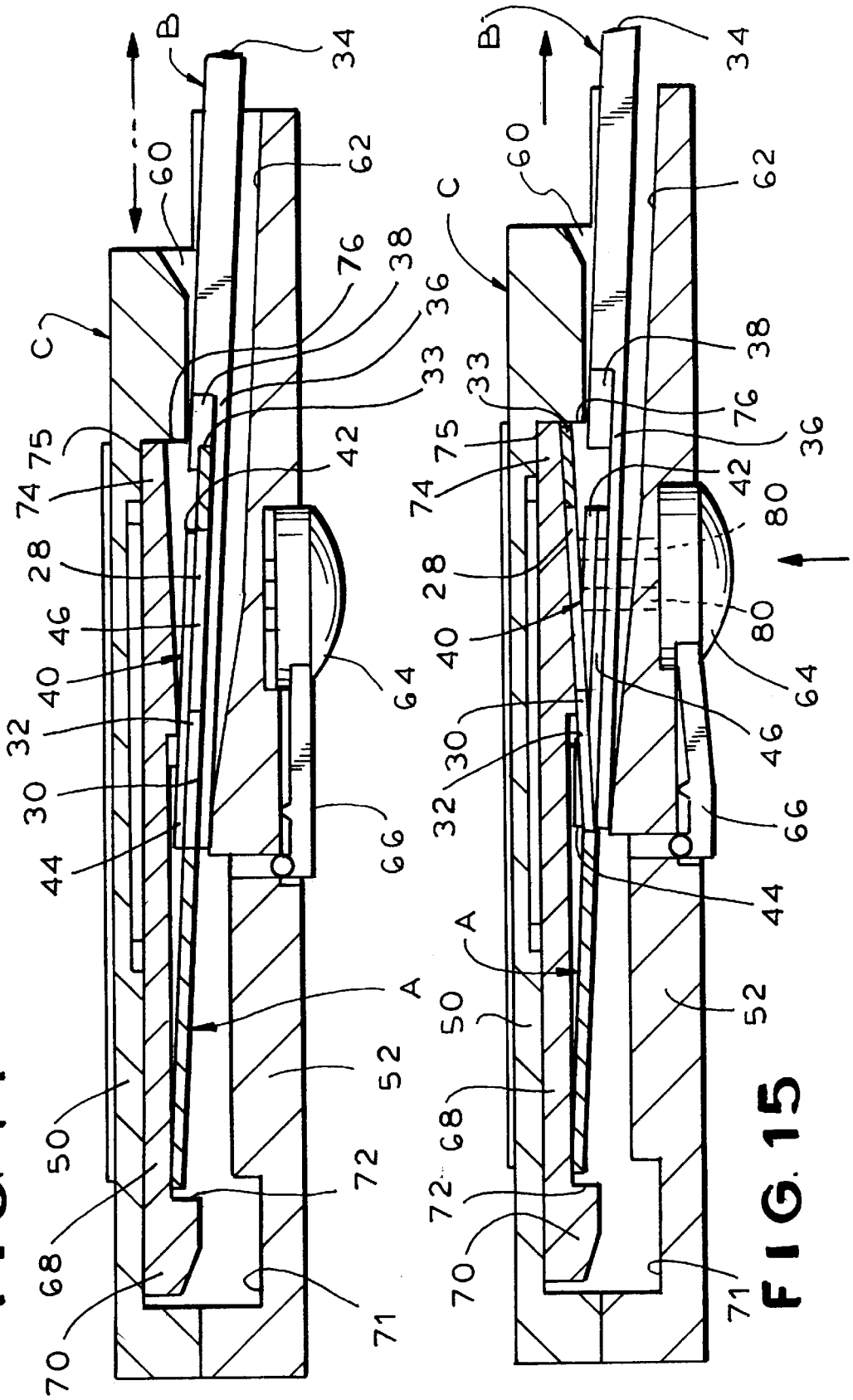

SURGICAL BLADE SYSTEM

BACKGROUND OF THE INVENTION

The present invention relates to surgical blade dispensing and disposal devices, and, in particular, to a system for blade removal and/or mounting for providing convenient storage, dispensing, and disposal of surgical blades of the type designed to be removeably mounted on a handle by means of a mating elongated slot and boss.

It is estimated that worldwide, some eighty five million surgical blades are used annually. Sterilized, stainless steel blades available in many sizes and orientations are designed to be mounted on reuseable handles. Most often, the blades are removed from sterile pouches and manually mounted on the handle. After use, contaminated blades are removed from the handle and discarded. Since the mounting and removal of the blade from the handle is done manually, there is potential for cutting and contamination of the personnel who change the blades.

Many attempts have been made to provide an inexpensive simple apparatus which minimizes the danger of being cut by a contaminated blade, provides for safe disposal and at the same time ensures the sterility of new blades. Providing devices for mounting and removing the blade from the handle without the necessity of touching them virtually eliminates the dangers involved. Typically, commercially available surgical blades have a sharpened tip, cutting edge portion and a shank portion extending rearwardly therefrom. The shank portion of the blade is provided with an elongated recess which is shaped and adapted to receive a mating elongated boss formed on the forward portion of a handle.

Generally, the elongated handle engaging recess of the blade can have a widened rear portion and a narrowed forward portion, the widened rear portion initially receiving the engaging boss of the scapel handle guiding the boss forward into the narrowed forward portion of the recess. The boss is undercut to form a slot such that the edges of the narrowed forward portion of the recess are engaged between a scapel handle and the slot formed by the undercut surface of the boss. When the boss is completely inserted within the blade recess, the rear edge of the blade recess can be snapped over the rear of the engaging boss, thus achieving locking engagement between the blade and the scapel handle.

In order to remove a blade of this nature from a scapel handle, the rear edge of the blade must be separated from the handle to disengage the rear end of the blade recess from the rear end of the boss so that the blade can then be pushed forward until the slot of the undercut boss clears the narrowed forward portion of the blade recess, permitting the blade to be cleared of the handle.

A sharp edge is essential in conducting a surgical operation. However, blades tend to lose their edge very quickly in such procedures so it is common to use several blades during a single surgical procedure. Thus, removal of a used blade from the handle and replacement of the blade with a new sterile blade is a frequent occurrence in the course of a surgical procedure.

The construction and operation of mounting and dismounting surgical blades on blade handles present problems in that the handling of such sharp blades for mounting and removal purposes can easily cause injury to the handler. Devices to eliminate handling of the blades have been developed.

For example, U.S. Pat. No. 3,172,316 to Grieshaber discloses a blade removing tool formed from tubing and having an elongated handle. One end is flattened somewhat so as to provide flat opposed surfaces in which are formed opposed channel-like grooves which function as guide tracks for the boss portion of the scapel when the tool and the scapel boss portion are assembled. Extending longitudinally from one flat surface of the flattened end portion of the handle are two spaced-apart prongs which are inclined upwardly a slight amount. The space between the prongs is such as to permit the slender boss portion of the scapel to pass therebetween, the free end of each prong being offset upwardly. The blade end of the scapel handle can be initially inserted longitudinally through the open flat end of the tube between the channel-like grooves. The offset ends of the tool prong slidably engaging the under surface of the blade until they engage behind the innermost edge of the blade adjacent the scapel handle. The inclination of the prongs cause the innermost edge portion of the accommodated blade to be flexed upwardly so that each edge portion thereof will clear the slender boss portion of the scapel when the scapel is withdrawn longitudinally from the flattened end of the tool. The blade of the scapel is held in place by the offset ends of the prongs during withdrawal of the scapel handle.

U.S. Pat. No. 4,180,162 to Magney shows a combination dispenser-disposal cartridge for a surgical blade which includes an elongated open-top box with means for receiving and positioning the blade in a curved position to accept the mating boss of a scapel handle. The box also includes means for stripping a used blade from the scapel handle and retaining it within the box for disposal. The blade is packed in the box so that it curvingly extends from the forward tip towards the shank tip to facilitate insertion of a boss of a scapel handle into the elongated slot, which is then moved forward and withdrawn with the blade mounted on the handle. Removal of the blade from the scapel handle is effected by inserting the scapel handle into the aperture end of the box until the tip of the blade is engaged between the side wall and a projection extending downwardly from the top of the box at which point the handle is moved to the right so that the rear edge of the blade is stripped away from the narrowed forward portion of the scapel handle by engagement against an upstanding blade disengaging projection formed integrally with the floor of the box. The Magney combination dispenser-disposal cartridge can prove to be somewhat ineffective in use resulting in surgeons or assistants resorting to manual removal of the blade from scapel handles.

Other devices include the scapel blade remover shown in U.S. Pat. No. 4,378,624 to Klingenberg which includes a fixed block in combination with a second movable block having a slot between such blocks and a tab provided on the movable block to engage an end of the blade and move it relative to the body of the blade to disengage it from the handle. The blocks are mounted on a supporting surface beneath which a sterile disposal box may be disposed.

U.S. Pat. No. 4,318,473 to Sandel shows a surgical blade removal and disposal device which operates by inserting a handle with a blade mounted thereon through a guide means so that the rear of the blade is disposed over spaced apart shoulders after which the handle is urged downward tending to bow the blade, thus disengaging the rear of the inserted portion from the rear edge of the blade slot to allow the handle to slide relative to the blade. The blade tends to move with the handle as a result of friction between the blade and the handle until it encounters the front wall of the stop which prevents further movement of the blade rearwardly. One of the problems encountered with the Sandel blade removal device is the severe bend imposed on the blade when it is fit over the spaced apart shoulders to guide the blade to the rear stop. This causes a high degree of friction between the blade slot and the handle boss making removal of the blade very difficult.

U.S. Pat. No. 4,344,532 to Eldridge, Jr., et al. discloses a surgical blade remover having a wedge shaped support member which tapers from its front side to its back side. The support has one or more mutually parallel latitudinal slots open at one end and along their length extending from the front side of the support to its interior. The slots are sized to receive the tang of the blade holder while preventing the blade itself from passing therethrough and the surface of each of the support members bordering the slot is covered with an adhesive which holds the blade in place while the handle is pivoted downward in the slot away from the blade. In certain embodiments, the slots are shown to have modifications contoured to compliment the shape of the blade and/or to provide a notch to receive a portion of the hilt of the blade in order to assist in blade removal.

U.S. Pat. No. 4,120,397 to Neumann discloses a unit for accommodating disposable blade-like articles in which the underside of a blade such as a scapel blade, slidably engages a resilient tongue-like element which is deflected upwardly. The tongue-like element has mounted thereon can means having surfaces which can be pushed against the blade to unseat the rear of the blade away from a boss on the blade handle. Once the tongue-like member is fully depressed thereby deflecting the rear of the blade downwardly, the scapel handle can be removed, abutting the rear of the blade against the inside surface of a panel, thus unseating the blade from the boss and disassembling the blade from the handle.

U.S. Pat. No. 4,106,620 to Brimmer, et al. shows a surgical blade dispenser and disposal assembly which includes blades individually positioned and supported within the box between a slot in a forward wall and a slot in a rearward wall which holds the blades in such a fashion as to slightly deform them in a lateral curve for receipt of a boss of a surgical blade holder in the elongated slot formed in the body of the blade. The blades can be removed by insertion of the blade bearings handle through the aperture and wedged rearwardly against projecting ears. The handle is then moved laterally to separate the rear of the blade from the boss and remove the handle completely off the blade. This device has proved to be cumbersome and the removal apparatus does not provide for efficient removal of the blades.

U.S. Pat. No. 4,746,016 to Pollak and Blasnik teaches a mechanism which can be used for both mounting and removing a blade having an elongated slot mounting means from a blade handle which has a mounting boss for insertion into the elongated slot. The mechanism includes a handle guide which forms one side of a passageway for insertion of the blade handle. The handle guide has a body portion which is sufficiently flexible to allow deflection of the handle for withdrawal of the boss out of mating relationship with the elongated slot of the blade. Another element of the mechanism is a blade extracting means fixed opposite the handle guide which forms a second side of the passageway. The extracting means has a blade retaining projection arranged adjacent the passageway which can be actuated to prevent withdrawal of a blade from the passageway. The mechanism also includes an actuation means fixed for actuation of the blade extracting means upon deflection of the handle sufficiently to disengage the boss out of a mating relationship with the elongated slot. As as consequence, a blade mounted on a handle can be removed when the handle is withdrawn from the passageway, while the extracting means is being actuated.

The Pollak apparatus has proven to be overly complex. Moreover, it requires that the handle be deflected from its original plane to dismount the blade from the handle, a movement which may be awkward to perform. The present system is a significant improvement over the Pollak structure because it is much simpler mechanically and includes a depressible button to dismount the blade from the handle.

It is, therefore, a prime object of the present invention to provide a surgical blade system in which surgical blades can be quickly and safely mounted onto a scapel handle.

It is another object of the invention to provide a surgical blade system which facilitates easy removal of the blade from a scapel handle.

Another object of the invention is to provide a surgical blade system with a stand which gives quick and easy access to a variety of surgical blades.

A further object of the present invention is to provide a surgical blade system which stores new surgical blades in a sterile manner.

Another object of the invention is to provide a surgical blade system which facilitates the safe disposal of used and contaminated scapel blades.

In accordance with one aspect of the present invention, a surgical blade system is provided comprising a handle having a blade mounting portion with a boss forming a slot. The blade has a boss receiving recess defined by an edge. A cartridge is adapted to removeably retain the blade. It has an opening adapted to receive the blade mounting portion of the handle as it is inserted into the cartridge. Spring means are located within the cartridge. The spring means has a surface abuting the blade. The spring means is normally in an arcuate state so as to retain the blade in a position wherein the recess edge can enter the handle slot. As the blade is moved by insertion of the handle, against the urging of the spring means, the edge moves into the slot and the boss is received within the recess to mount the blade on the handle.

Means actuatable from the exterior of the cartridge are provided to move the blade relative to the blade mounting portion to dismount the blade from the handle. The actuatable means comprises a pushbutton and a protrusion extending from the pushbutton and adapted to move the blade when the pushbutton is depressed. The protrusion extends in a direction substantially perpendicular to the plane of the blade when the blade is mounted on the handle. The actuatable means preferably comprises first and second spaced protrusions adapted to engage the blade at opposite sides of the boss receiving recess.

The initial position of the blade is at an acute angle with the blade mounting portion of the handle. More specifically, the initial blade position is in a plane which forms an acute angle with the plane of the blade mounting portion of the handle. The final position of the blade is coplanar with the plane of the blade mounting portion of the handle.

The arcuate spring means is mounted to the cartridge interior in cantilever fashion. It includes means for limiting the movement of the blade relative to the spring means. The limiting means comprises a surface against which the tip of the blade abuts.

The cartridge comprises a section into which the spring means extends. A knurled exterior surface is provided on that section to facilitate handling of the cartridge.

The handle comprises an inclined surface. The blade has a correspondingly inclined mating surface. The cartridge has indicia thereon corresponding to the inclined handle surface.

The cartridge opening is defined by a handle guide surface. The handle guide surface is substantially parallel to the plane of the final position of the blade.

In accordance with another aspect of the present invention, the surgical blade system includes a handle having a blade mounting surface with a raised boss forming a slot with an entrance. A blade is provided with a boss receiving recess defined by an edge. A cartridge is adapted to removeably retain the blade. It has an opening adapted to receive the blade mounting portion of the handle. Spring means are mounted in cantilever fashion within the cartridge. The spring means normally maintains the blade in a plane which forms an acute angle with the plane of the handle. In that position, the blade edge is aligned with the slot entrance. Insertion of the handle causes the blade to move, against the urging of the spring means, toward the plane of the handle. This permits the blade edge to move within the slot and the boss to be received within the recess to mount the blade on the handle.

The spring means is normally in an arcuate state. The spring means changes to a straightened state as the blade is moved by insertion of the handle. The final position of the blade is coplanar with the plane of the handle.

In accordance with another aspect of the present invention, a holder for one or more blade containing cartridges is provided. Each of the cartridges has an exterior blade release button. The holder includes a housing. Means are provided for retaining the cartridge within the housing. The retaining means comprises a rigid finger aligned with the pushbutton. Exertion of a force on the cartridge in the direction of the finger causes the finger to actuate the blade release button.

To these and to such other objects which many hereinafter appear, the present invention relates to a surgical blade system, as set forth in detail in the following specification and recited in the annexed claims, taken together with the accompanying drawings, in which like numeral refer to like parts, and in which:

FIG. 1 is a plan view of one side of the cartridge and a portion of the handle of the system of the present invention;

FIG. 2 is a plan view of the other side of the cartridge and handle portion illustrated in FIG. 1;

FIG. 3 is a top elevational view of the cartridge and handle portion illustrated in FIG. 1;

FIG. 4 is a cross-sectional view taken along line 4—4 of FIG. 3;

FIG. 5 is a cross-sectional view taken along line 5—5 of FIG. 3;

FIG. 6 is a view similar to FIG. 4 but showing the handle fully inserted into the cartridge;

FIG. 7 is a view similar to FIG. 5 but showing the handle fully inserted into the cartridge;

FIG. 8 is a cross-sectional view taken along line 8—8 of FIG. 7;

FIG. 9 is a cross-sectional view taken along line 9—9 of FIG. 7;

FIG. 10 is a view similar to FIG. 4 showing the handle carrying a blade being withdrawn from the cartridge;

FIG. 11 is a view similar to FIG. 5 showing the handle with a blade being withdrawn from the cartridge;

FIG. 12 is an enlarged cross-section view taken along line 12—12 of FIG. 1;

FIG. 13 is an enlarged cross-sectional view similar to that of FIG. 12 showing the blade edge as it enters the handle slot;

FIG. 14 is an enlarged cross-sectional view similar to that of FIG. 12 showing the boss seated within the handle slot;

FIG. 15 is an enlarged cross-sectional view similar to that of FIG. 12 showing the pushbutton being depressed to dismount the blade;

Figure 16:
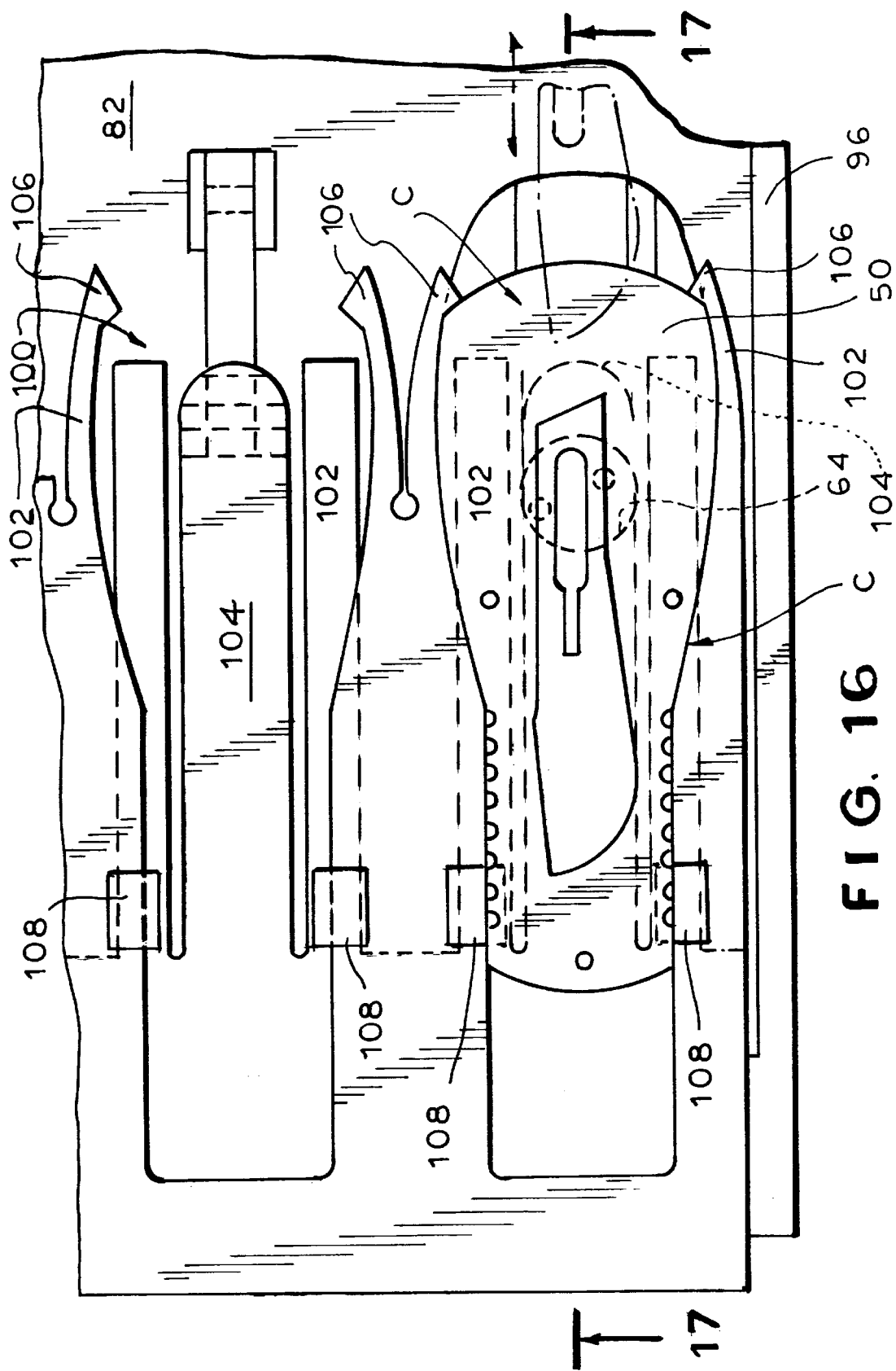
FIG. 16 shows a top view of a portion of the stand housing showing two cartridge receiving openings, one of which has a cartridge retained therein.

The surgical blade system of the present invention includes a disposable blade, generally designated A, a handle upon which blade A is adapted to be removeably mounted, generally designated B, and cartridge, generally designated C. Cartridge C retains blade A in a sterile manner prior to mounting on handle B and receives blade A for safe disposal after it is dismounted from handle B. Cartridge C contains a mechanism which permits mounting and dismounting of the blade on the handle without any direct contact with the blade by the user.

Blade A includes a cutting portion 20 with an arcuate cutting edge 22 and a mounting portion 24 with an elongated recess 26. Recess 26 has a larger rear portion 28 and a smaller forward portion 30 defined by an edge 32. The rear edge 33 of blade A is inclined.

Handle B has a grip portion 34 and a blade mounting portion 36 separated by an inclined surface 38. One surface of blade mounting portion 36 carries a raised boss 40 which has a wider rear portion 42 and a narrower front portion 44. Portion 44 defines, as is best seen in FIG. 8, a slot 46 which is adapted to receive edge 32 of blade A. When mounted on handle B, front portion 44 of the boss will be situated within recess portion 30 and rear portion 42 of the boss will be received within recess portion 28 with the blade and handle coplanar. Surface 33 of blade A will abut surface 38 of handle B.

Cartridge C comprises a plastic housing including a first side section 50 and a second side section 52 which are joined together by three screws 54. When assembled, sections 50 and 52 form a hollow enclosure with a grip portion 56 having a knurled edges 58 and a handle entrance opening 60 defined in part by a guide surface 62, which is situated on section 52. A pushbutton 64 is accessible from the exterior of section 52 and held in place by a living hinge 66.

Located within cartridge C is provided a flat metal spring element 68 which is mounted to the interior wall of the cartridge in cantilever fashion. Spring 68 has an unattached end 70 which is provided with a shoulder defining a tip limiting surface 72. The other end 74 of the spring is permently attached to the interior wall 75 of the housing section 50. End 70 of spring 68 is normally received within a recess 71 in side 52, when spring 68 is in its normal arcuate state (FIG. 12).

Spring 68 is moved by blade A within the hollow cartridge between a normal, fully arcuate state, shown in FIG. 12, through an intermediate state, shown in FIG. 13, to a straightened state, shown in FIG. 14, as the handle is inserted into the cartridge, in order to mount the blade on the handle.

As seen in FIG. 12, spring 68 in its arcuate state maintains blade A in a plane which forms an acute angle with guide surface 62 and thus the plane of handle B. Blade A is prevented from moving in one direction relative to end 70 of the spring 68 by surface 72 and from moving in the other direction by surface 76. Surface 76 is adjacent and perpendicular to the interior wall 75 of section 50 to which end 74 of spring 68 is affixed.

As the handle is inserted in opening 60 and pushed along guide surface 62, it bears against blade A and spring 68 is moved from its fully arcuate state to the intermediate state such that edge 32 defining recess portion 30 enters slot 46 defined by the raised boss 40. As the handle continues to move along guide surface 62, blade A causes spring 68 to move to a straightened state, the leading portion of the boss 40 moves down the narrow portion 30 of the recess 28 and the following portion 42 of the boss lodges in the wider portion 28 of the recess such that the blade and handle are coplanar, as illustrated in FIG. 14. The blade is now mounted on the handle. The handle can be withdrawn from the cartridge and used.

After the blade is used, the handle with the used blade thereon is reinserted into opening 60 in cartridge C until the tip of the blade abuts limiting surface 72 on spring 68. To dismount the blade, pushbutton 64 is depressed. Pushbutton 64 is mounted in a recess on the surface of section 52. A pair of spaced protrusions 80 extend from the bottom of pushbutton 64, at positions aligned with points on blade A on either side of recess 26, see FIGS. 2 and 15. Depressing the pushbutton causes protrusions 80 to engage the surface of blade A and move the blade out of the plane of handle B (FIG. 15) so as to dismount the used blade from the handle. The handle can then be withdrawn from the cartridge while the blade remains lodged in the cartridge between surfaces 72 and 76. The cartridge, containing the used blade, can be safely discarded.

Figure 17:
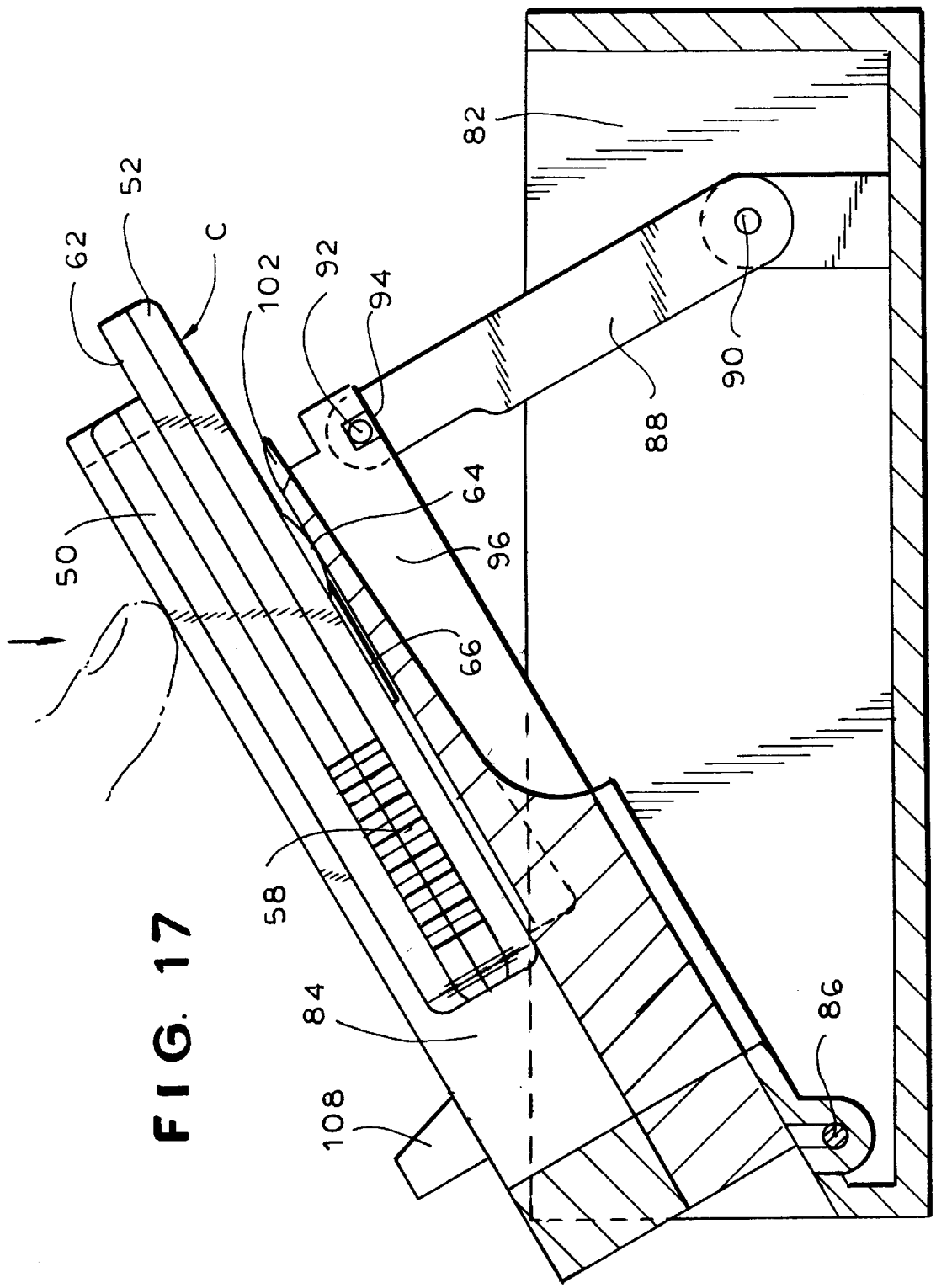
FIG. 17 is a side elevational view of the stand.

FIGS. 16 and 17 illustrate a dispensing stand designed for use with one or more of the cartridges C. The stand consists of a box-like base 82. Within base 82, a plate 84 is pivotally mounted by hinge 86. A lever 88 is also pivotally mounted within base 82 by a hinge 90. The free end of lever 88 carries a shaft 92 which is adapted to be received within a recess 94 on side 96 of plate 84 to retain plate 84 at an acute angle (for example, 30°) with the base.

Plate 84 consists of one or more cartridge receiving recesses 100, two of which are shown in FIG. 16. Each recess 100 is defined by a first and second side spring clamp arms 102 and a rigid support finger 104. Arms 102 are made of resilient material and shaped to cam open to receive a cartridge C and thereafter return to their original position where the enlarged ends 106 abut the rear edge of side 50 of cartridge C to securely retain the cartridge. Arms 102 can be spread apart to release the cartridge by manipulating tabs 108. Finger 104 is aligned with pushbutton 64 when the cartridge is received in the recess.

To release a blade from a handle, the pushbutton 64 of the cartridge is depressed by a force applied to the exterior of side 50 of the cartridge (as shown in FIG. 17) in the direction of the finger. This causes the pushbutton to depress and blade to be dismounted from the handle. The handle can then be withdrawn form the cartridge. The cartridge, with the used blade, is released from the stand by pushing tabs 108 away from each other to spread arms 102.

Cartridges containing the same or different size blades can be packaged with the stand. Alternatively, the cartridges can be removed from a sterile pack and inserted into the stand prior to use. Stands capable of accomodating four or more cartridges are preferred.

It will now be appreciated that the present invention relates to a surgical blade system which permits quick and safe mounting and dismounting of a blade on a handle. The blades are maintained in a sterile condition until used. Contaminated blades can be disposed of without exposing the user.

The system includes a blade retaining cartridge. Insertion of the handle into the cartridge causes a normally arcuate spring to straighten to mount the blade. The handle with the blade is withdrawn and the blade used. To dismount the used blade, the handle and blade are reinserted into the cartridge and the pushbutton is depressed. This causes the blade to dismount from the handle so the handle can be withdrawn. The contaminated blade remains safely within the cartridge.

While only a single embodiment of the invention has been disclosed for purposes of illustration, it is obvious that many variations and modifications could be made thereto. It is intended to cover all of these variations and modifications which fall within the scope of the invention, as defined by the following claims:

We claim:

1. A surgical blade system comprising a handle having a blade mounting portion with a surface with a raised boss forming a slot, a blade with a boss receiving recess defined by an edge and a cartridge adapted to removeably retain said blade and having an opening adapted to receive said blade mounting portion of said handle as said handle portion is inserted into said cartridge, spring means mounted within said cartridge having a surface abuting said blade, said spring means normally being in an arcuate state so as to retain said blade in a position wherein said edge is aligned with said slot, said blade being moveable by insertion of said handle, against the urging of said spring means, such that said edge moves into said slot and said boss is received within said recess to mount said blade on said handle.

2. The system of claim 1 wherein said blade is retained at an acute angle relative to said blade mounting portion of said handle when said spring means is in said arcuate state.

3. The system of claim 1 wherein said blade is moved by insertion of said handle to a position coplanar with the plane of said blade mounting portion surface.

4. The system of claim 1 wherein said blade is retained in a plane which forms an acute angle with respect to the plane of said blade mounting portion when said spring means is in said arcuate state.

5. The system of claim 1 further comprising means actuatable from the exterior of said cartridge to move said blade relative to said blade mounting portion to dismount said blade from said handle.

6. The system of claim 5 wherein said actuatable means comprises a pushbutton.

7. The system of claim 6 wherein said actuatable means comprises a protrusion extending from said pushbutton, said protrusion moving said blade relative to said blade mounting portion when said actuatable means is actuated.

8. The system of claim 7 wherein said protrusion is moved in a direction substantially perpendicular to the plane of said blade when said blade is coplanar with said blade mounting portion.

9. The system of claim 6 wherein said actuatable means comprises first and second spaced protrusions adapted to engage said blade at points on opposite sides of said boss receiving recess.

10. The enclosure of claim 1 further comprising a surface substantially parallel to the plane of said blade mounting portion.

11. The system of claim 1 wherein said blade has a tip and wherein said spring means comprises means for limiting the movement of the tip of said blade relative to said spring means.

12. The system of claim 11 wherein said limiting means comprises a surface against which the tip of the blade abuts.

13. The system of claim 1 wherein said cartridge comprises a section with an exterior into which said spring means extends, said section exterior comprising a knurled surface to facilitate holding of said cartridge.

14. The system of claim 1 wherein said handle comprises an inclined surface and said blade has a correspondingly inclined surface.

15. The system of claim 14 wherein said cartridge has an exterior surface with indicia thereon corresponding to said inclined handle surface.

16. The system of claim 1 wherein said cartridge opening is defined by a handle guide surface.

17. The system of claim 1 further comprising means for mounting said spring means within said cartridge in cantilever fashion.

18. The system of claim 1 wherein said spring means is a flat spring.

19. The system of claim 1 wherein said spring means assumes a substantially straightened state when said blade is in a position coplanar with that of said blade mounting portion.

20. A surgical blade system comprising a handle having a blade mounting surface with a raised boss forming a slot with an entrance, a blade with a boss receiving recess defined by an edge and a cartridge adapted to removeably retain said blade and having an opening adapted to receive said blade mounting surface of said handle, spring means mounted in cantilever fashion within said cartridge, said spring means normally maintaining the blade in a plane forming an acute angle with respect to the plane of said handle, wherein said edge is aligned with said slot entrance, insertion of said handle causing said blade to move against the urging of said spring means, toward the plane of said handle, to permit said edge to move within said slot such that said boss is received within said recess to mount said blade on said handle.

21. The system of claim 19 wherein said spring means is normally in an arcuate state.

22. The system of claim 20 wherein said spring means assumes a straightened state as said blade is moved toward the plane of said handle.

23. The system of claim 21 wherein said blade moves from a position which forms an acute angle with the plane of said handle toward a position which is coplanar with the plane of said handle.

* * * * *